US007494221B2

(12) United States Patent
Turovetsky

(10) Patent No.: US 7,494,221 B2
(45) Date of Patent: Feb. 24, 2009

(54) METHOD FOR PREVENTING DETERIORATION OF THE SENSE OF SIGHT AND/OR FOR MENDING THE SENSE OF SIGHT OF USERS OF DISPLAY FACILITIES

(76) Inventor: Vladimir Naumovich Turovetsky, Elektrougly, Pl. Oktyabrya 3-34, 142490, Moskovskaya Obl. (RU)

( * ) Notice: Subject to any disclaimer, the term of this patent is extended or adjusted under 35 U.S.C. 154(b) by 959 days.

(21) Appl. No.: 10/258,779

(22) PCT Filed: Apr. 20, 2001

(86) PCT No.: PCT/RU01/00164

§ 371 (c)(1),
(2), (4) Date: Feb. 26, 2003

(87) PCT Pub. No.: WO01/80808

PCT Pub. Date: Nov. 1, 2001

(65) Prior Publication Data

US 2003/0156254 A1 Aug. 21, 2003

(30) Foreign Application Priority Data

Apr. 27, 2000 (RU) ............................. 2000110582

(51) Int. Cl.
*A61B 3/00* (2006.01)

(52) U.S. Cl. ...................................................... 351/203

(58) Field of Classification Search ................. 351/203, 351/237, 239, 246, 247, 200
See application file for complete search history.

(56) References Cited

U.S. PATENT DOCUMENTS 3,855,998 A * 12/1974 Hidalgo-Briceno ......... 600/545
5,304,112 A * 4/1994 Mrklas et al. ................. 600/27
5,515,069 A * 5/1996 Dillon, III ....................... 345/6
6,072,443 A * 6/2000 Nasserbakht et al. ........... 345/7
6,102,846 A * 8/2000 Patton et al. .................. 600/26
6,306,077 B1 * 10/2001 Prabhu et al. ................. 600/26
6,364,485 B1 * 4/2002 Fateh ......................... 351/203
6,483,485 B1 * 11/2002 Huang et al. .................. 345/10
6,798,898 B1 * 9/2004 Fedorovskaya et al. ..... 382/128

FOREIGN PATENT DOCUMENTS

| | | |
|---|---|---|
| RU | 2077292 | 4/1997 |
| RU | 10069 U1 | 6/1999 |
| RU | 2134053 | 8/1999 |
| RU | 2147763 | 4/2000 |

OTHER PUBLICATIONS

A.A. Feigin et al, “Application of Spectral Filter Glasses by Display Users,” (journal Opthamology News), No. 6, 23, 1997, pp. 12-17, correct title is “Human Physiology”.

* cited by examiner

*Primary Examiner*—Hung X Dang
(74) *Attorney, Agent, or Firm*—Collard & Roe, P.C

(57) ABSTRACT

The invention relates to medicine. The inventive method consists in influencing the user’s eyes by additional pictures on screen, whereby an image is formed whose shape and color range have a relaxing effect on a visual analyzer. The duration of exposure to the additional pictures are selected in such a way that they perform a relaxing effect on lateral and transversal eye muscles. The time interval between the images range from 20 to 150 min, the duration of exposure is selected within a range of 1.0 to 6.0 min. Together with the relaxing effect on a visual organ, said relaxing action is also exerted on an organ of hearing and muscles of the neck. The shape of at least a part of the additional pictures is smooth and roundish without distinct lines and boundaries.

3 Claims, 12 Drawing Sheets
(11 of 12 Drawing Sheet(s) Filed in Color)

METHOD FOR PREVENTING DETERIORATION OF THE SENSE OF SIGHT AND/OR FOR MENDING THE SENSE OF SIGHT OF USERS OF DISPLAY FACILITIES

CROSS REFERENCE TO RELATED APPLICATIONS

Applicant claims priority under 35 U.S.C. §119 of Russian Application No. 2000110582, filed Apr. 27, 2000. Applicant also claims priority under 35 U.S.C. §365 of PCT/RU01/00164 filed Apr. 20, 2001. The international application under PCT article 21(2) was not published in English.

FIELD OF INVENTION

The invention relates to medicine, more precisely to hygieology and ophthalmology, and can be used for preventing deterioration of the sense of sight and improving the sense of sight of a person reading images off the screen of a video device, such as a computer, television set and the like.

STATE OF THE ART

Numerous studies have shown that prolonged viewing of a video device screen can cause such changes in the visual organ as onset or progress of existing myopia.

Such changes are related to the specifics of screen images (self-luminous, low contrast, discrete and flickering), which are very tense and even stressful for the human eye to read off, and during computer operation requiring the eye to continually shift from the screen to the keyboard and the text printout. Efforts to prevent deterioration of eyesight are to be, therefore, applied to the refraction system, that is, optical adjustment of the eye to direction of light, and accommodation, that is, adjustment of the eye to different distances. Besides, it has been confirmed that screen images affect the central nervous system (CNS) through the visual organ and produce excitation foci in the CNS.

Various devices are used today to prevent deterioration of eyesight caused by viewing images on the computer display screen, such as using dioptrically corrected eyeglasses or specially tinted contact lenses. Known in the art is a method to improve eyesight with the aid of glasses provided with a computer-designed spectral filter that improve color discrimination and color contrast and make the image on the retina clearer and more contrasting (A. A. Feigin, P. P. Zak, T. A. Korniushina, J. Z. Rosenblum, L. I. Nesteriuk, and P. E. Golikov, "Application of Spectral Filter Glasses by Display Users," journal *Human Physiology*, No. 6, 23, 1997, pp. 12-17). Glasses also help reduce image "pixelization" on the screen, "adjust" the screen radiation spectrum to maximum spectral sensitivity of eye photoreceptors, improve accommodation ability, reduce useful signal detection time, and cut out the shortwave hard part of the spectrum that adversely affects the optical media of the eye.

Regardless of the foregoing advantages of the prior art method using a computer-designed spectral filter, it is basically inconvenient because of the need to wear eyeglasses all the time.

It is an object of this invention to develop a comfortable method to prevent deterioration of vision and/or to improve vision without using any additional devices such as eyeglasses, contact lenses, and so on.

ESSENCE OF THE INVENTION

The technical effect of this invention consists in improving comfort and reliability of the preventive technique by periodically applying a relaxing effect on the visual organ during the entire screen image viewing period. Besides, it is possible to provide an additional relaxing effect on the CNS through the visual organ, that is, relieving the excitation foci caused by continuous physical and emotional load.

The technical effect is achieved by a method of preventing deterioration of sense of sight and/or improving sense of sight of video device users, comprising applying an additional effect to the user's eyes, the said additional effect is achieved by exposing the user to additional images on the screen of an image-forming device, the shape and color range of which produces a relaxing effect on the visual analyzer, the duration of additional image exposure being organized, long enough to restore the content of adenosine triphosphate and oxygen in the eye tissues, and the time intervals between image exposures being organized, shorter than the time intervals sufficient for tissue acidulation to set in and hypoxia to occur.

Moreover, the user is exposed to such additional images, the shape and color range of which has a relaxing effect on the visual analyzer region in the central nervous system (CNS).

The shape and color range of the additional images that have a relaxing effect on the visual analyzer are selected in such a way that they have a relaxing effect on accommodation and rectus and oblique muscles of the eye.

Moreover, the time intervals between image exposures ar selected within a range of 20 to 150 minutes, and the duration of additional image exposure on the screen is selected within a range of 1.0 to 6.0 minutes.

A relaxing effect can be applied to the hearing organ and/or neck muscles simultaneously with the relaxing effect on the visual organ.

It is preferred for the shape of at least some of the additional images to be smooth and rounded, and for the shape of at least some of these images to be without distinct transition line and boundaries. The color range of images exerting an effect on the CNS is black and white, and the primary color range of images exerting an effect on the visual analyzer is yellow and green.

Additional images are used in the form of a program built into computer programs such as Microsoft Word, Microsoft Windows or Microsoft Excel, or Internet Explorer, or Netscape Navigator, or any other.

Additional images can be displayed on the screen simultaneously with the foreground image, in which case the additional images of non-transparent and/or saturated colors are to be displayed beyond the boundaries, right and/or left at the side of the screen working area, where they can be transformed into transparent images as the cursor is moved toward and/or over them, while additional transparent and/or saturated color images are created in any part of the screen and can change the color of the text and/or graphics of the main program.

Simple figures and/or complex images, such as flowers or animals, or others, are preferably to be used as additional images.

The method of this invention can be performed with a specialized computer program or an animation film.

Considering the average screen exposure of eight hours a workday and the physiological laws of the human organism, it was proposed to develop a computer programs comprising 10 vignettes with special images lasting 3 to 5 minutes each, to be displayed on the computer screen every 30 to 50 minutes of work time. Moreover, the vignettes differ from one another in their effect on the human organism.

Numerous studies have confirmed, in the first place, the importance of a relaxing effect on the CNS, that is, relief of excitation foci caused by continuous physical and emotional work during the preceding period.

The effect on accommodation is required under all circumstances. It is also required to exert a relaxing effect on the external muscles of the eyes.

The effect on the system comprising the CNS, the visual organ and the external muscles is to strictly comply with the physiological laws of the organism, taking account of experimental results supporting these laws.

First, relaxing vignettes are to be displayed on the screen exactly at specified time intervals, which optimally range from 30 to 50 minutes of work. Second, duration of a vignette is not to exceed six minutes (optimally, it is to be 3 to 5 minutes). Third, each vignette performs its strictly defined function of exerting a certain effect on the organism. Fourth, each successive vignette differs from the preceding one. Fifth, the vignettes are to use a strictly specified color range. Sixth, the images of objects or pictures in the vignettes are to have smooth and rounded shapes, without sharp-edge outlines and boundaries. In a further modification, a vignette can be accompanied by music such as sounds of living creatures in nature, for it has been demonstrated that an additional effect on the hearing analyzer improves the efficiency of the relaxing effect on the human organism.

It has been shown that black-and-white lattices of contrast varying in spatial frequency are optimal stimuli for the basic functions of cortical receptive fields. It has been established that a neuron provides a full response to a moving lattice of particular dimensions. It has also been found that the orientation and spatial frequency of bands is no less important a factor. Accommodation is affected by images in the range of yellow and light-blue colors, greens being a possible option. The external muscles of the eye are affected by the direction and repetition rate of images moving on the screen.

When a person works on a computer or watches a television program, the external muscles of his or her eyes experience prompt adaptation, that is, lactic acid rapidly accumulates in the external muscles, causing tissue acidulation and hypoxia. This is a damaging reaction that can be corrected by changing prompt adaptation to long-term adaptation. As adaptation proceeds, neurohumoral regulation occurs. After a sequence of properly selected training sessions, the organism begins to respond to training in a more economical way, because each successive training session takes place at a super-compensation stage.

This effect is achieved by selecting intervals between vignettes so that they end before tissue acidulation begins and tissue hypoxia sets in as a result of lactic acid accumulation, and exposure duration of each vignette is selected to allow the content of adenosine triphosphate (ATP) and oxygen in the visual organ to be restored.

The specified time intervals are determined experimentally by existing direct methods, such as measuring the-content of lactic acid (or lactate), oxygen shortage and ATP concentration in the blood at specified time intervals for eyes under load, that is, during screen exposure, and at rest. Measurements and time interval determination can be made individually for each user, or else a series of measurements can be taken and average values determined.

This method also helps improve the sense of sight, because it exerts an effect on, first, the external and internal muscles of the eyes by applying a regular and measured action to the eyes, improving blood circulation in the muscles, activating their metabolic processes, improving the trophic function to make them more economical, and increasing the reserves needed for a more prolonged work. The central nervous system is affected by the program using different-colored vignettes, or the so-called color therapy. This action causes fusion of pathological excitation foci in the central nervous system, which always occur during prolonged work in front of a display screen. A person's general emotional background improves under the effect of positive images. This comprehensive effect on the visual organ helps stimulate its functions and improve the sense of sight.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings.

DESCRIPTION OF A PREFERRED EMBODIMENT OF THE METHOD

Program for Applying a Systemic Corrective Effect to the Visual Organ to Relax It During Computer Operation Ten vignettes of three minutes each. A total of 30 minutes.

1. Effect on the CNS

White general background. Several black bands extend vertically at equal intervals from one another. Bands of a smaller diameter are placed on two sides relative to them, and still smaller bands are provided at their sides relative to them, and so on, until the intervals between all the bands are equal. Smaller bands converge in a "concertina" fashion on the central band and expand back to their original position.

2. Effect on the CNS

As above, in a horizontal plane.

3. Effect on the CNS

White general background. The topmost row consists of the largest raindrops. In the descending rows below, raindrops decrease progressively in size, being of the same size in each individual row. The raindrops have a gray background. At the start of work, the topmost layer is black, and after a while the next lower row turns black, and the topmost row becomes gray again, and so on.

4. Effect on Accommodation

Four green “daisies” are placed against a yellow background. Movement occurs within the “daisies”, color intensity changing from center to periphery and back.

5. Prevention of accommodative strabismus (effect on the internal and external rectus and oblique muscles)

A green general background. Two rows of spheres of all spectrum colors facing one another in the center. All the spheres move in a vertical row in opposite directions away from one another, to reappear in the center of the screen again.

6. Effect on the Oblique Muscles of the Eyes

A yellow general background. An irregular green figure eight appears in the center of the screen, extending diagonally, its top loop being significantly larger than its bottom loop. The color intensity of the figure changes from bottom up in such a way that after one color fills the figure completely, another color appears at the beginning of the figure.

7. Effect on the Oblique Muscles of the Eyes

As in 6, except that the figure eight is a mirror reflection of the preceding figure eight.

8. Effect on the Lower and Upper Rectus Muscles of the Eyes

A light-blue general background. Several identically yellow-colored figures of eight of identical size are arranged in a vertical plane. Color intensity changes from top down.

9. Effect on the Lower and Upper Rectus Muscles of the Eyes

As in 8, except that color intensity changes from top down.

10. Effect on Accommodation

A yellow general background. Two light-blue circles, with two intense-green circles placed in their centers, are located parallel to one another against this background. Dark-blue circles move out and in.

It is advisable to take a Luscher test or any of its modifications at the end of computer session.

INDUSTRIAL APPLICABILITY

This method can be implemented with the aid of a computer program or animation film that can be produced in quantity.

Figure 1:
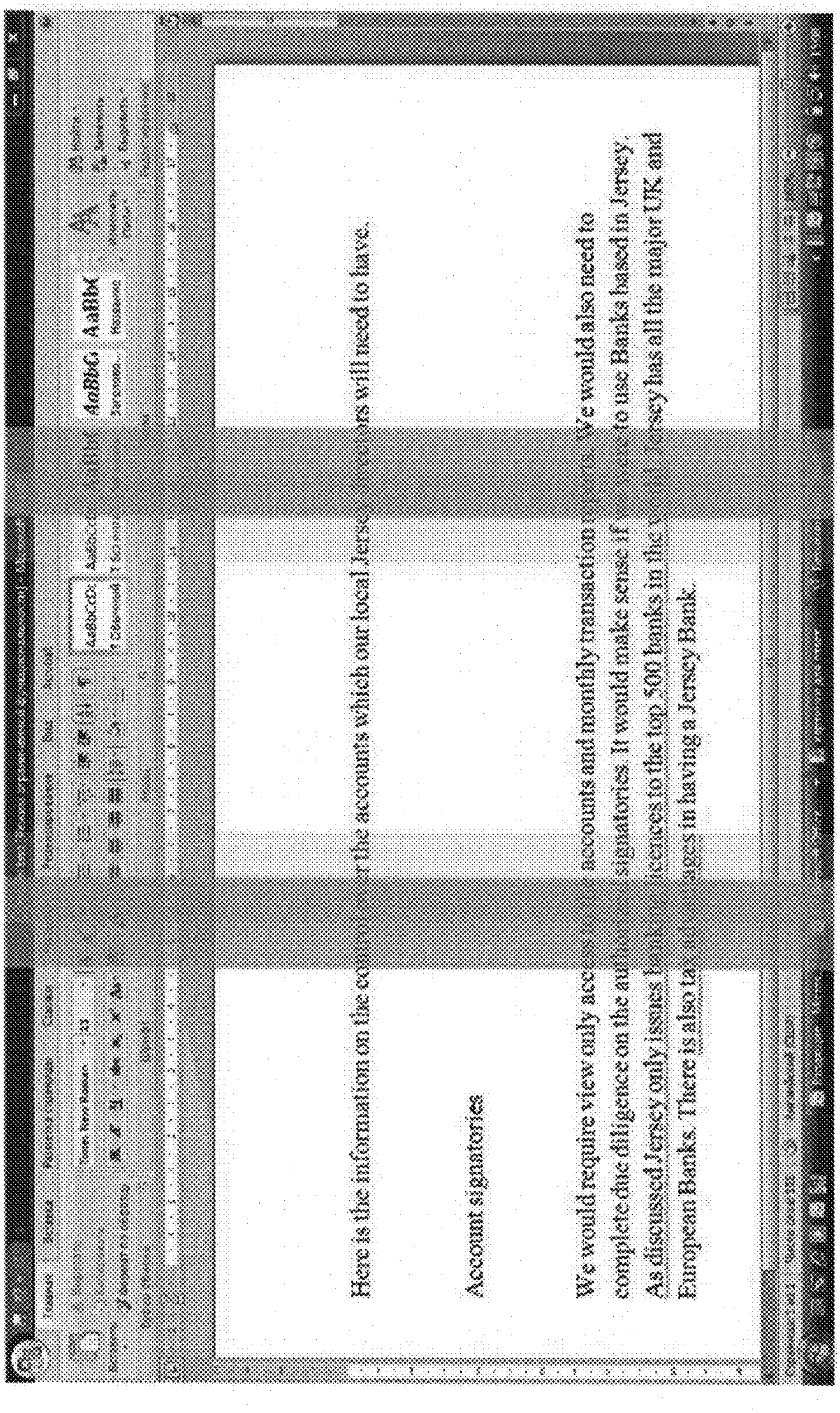
FIG. 1 shows a first embodiment in color for the invention.
Figure 2:
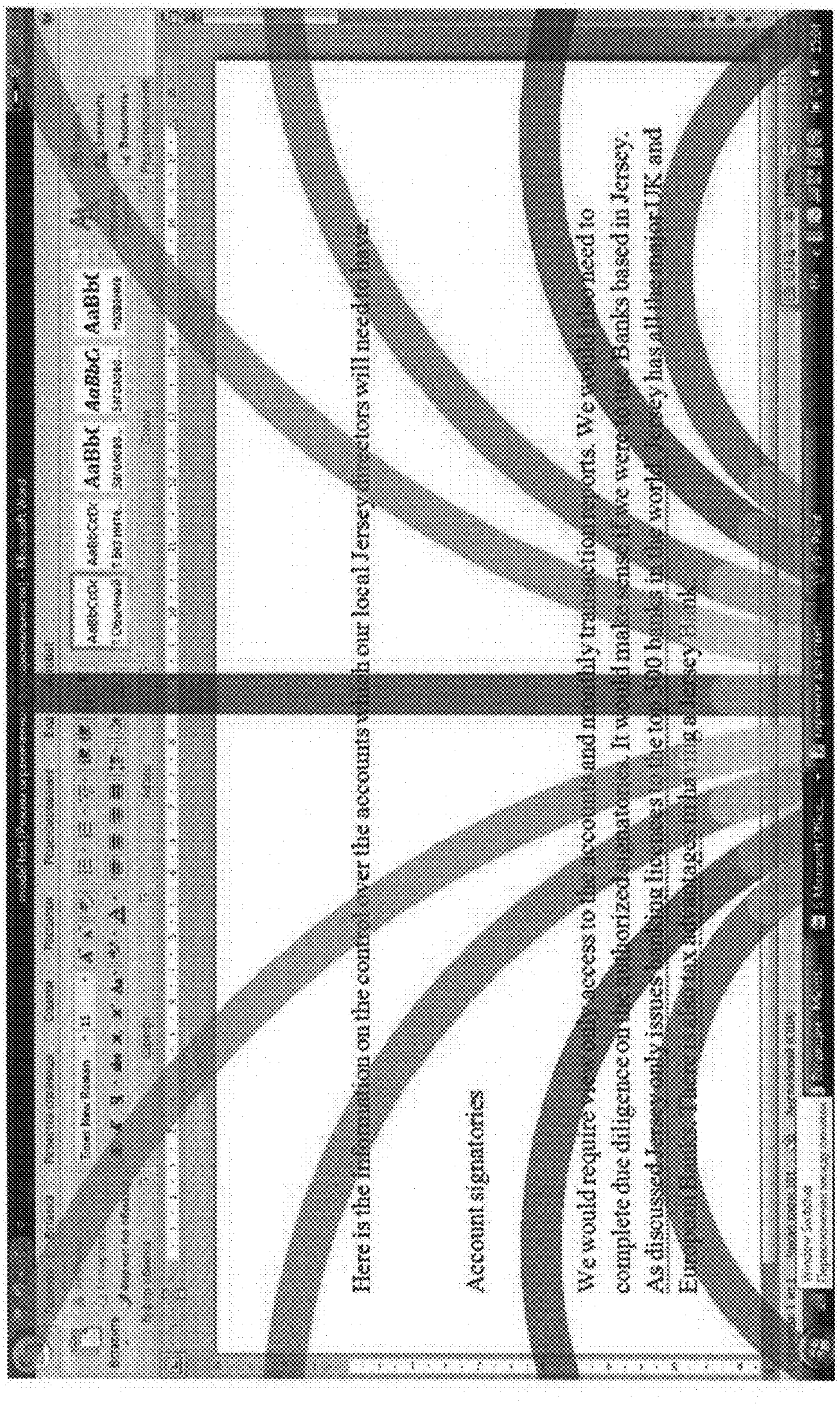
FIG. 2 shows a second embodiment in color for the invention.
Figure 3:
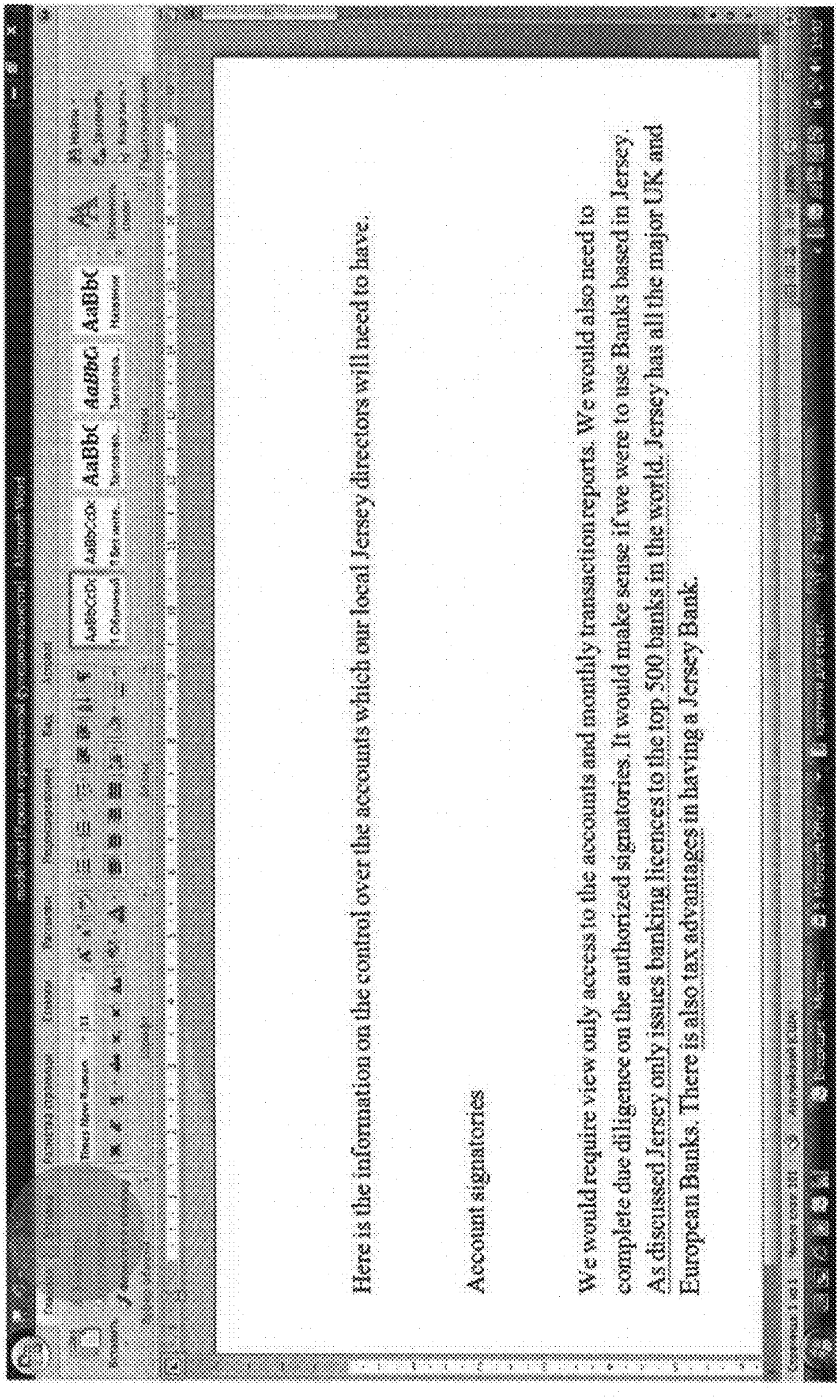
FIG. 3 shows a third embodiment in color for the invention.
Figure 4:
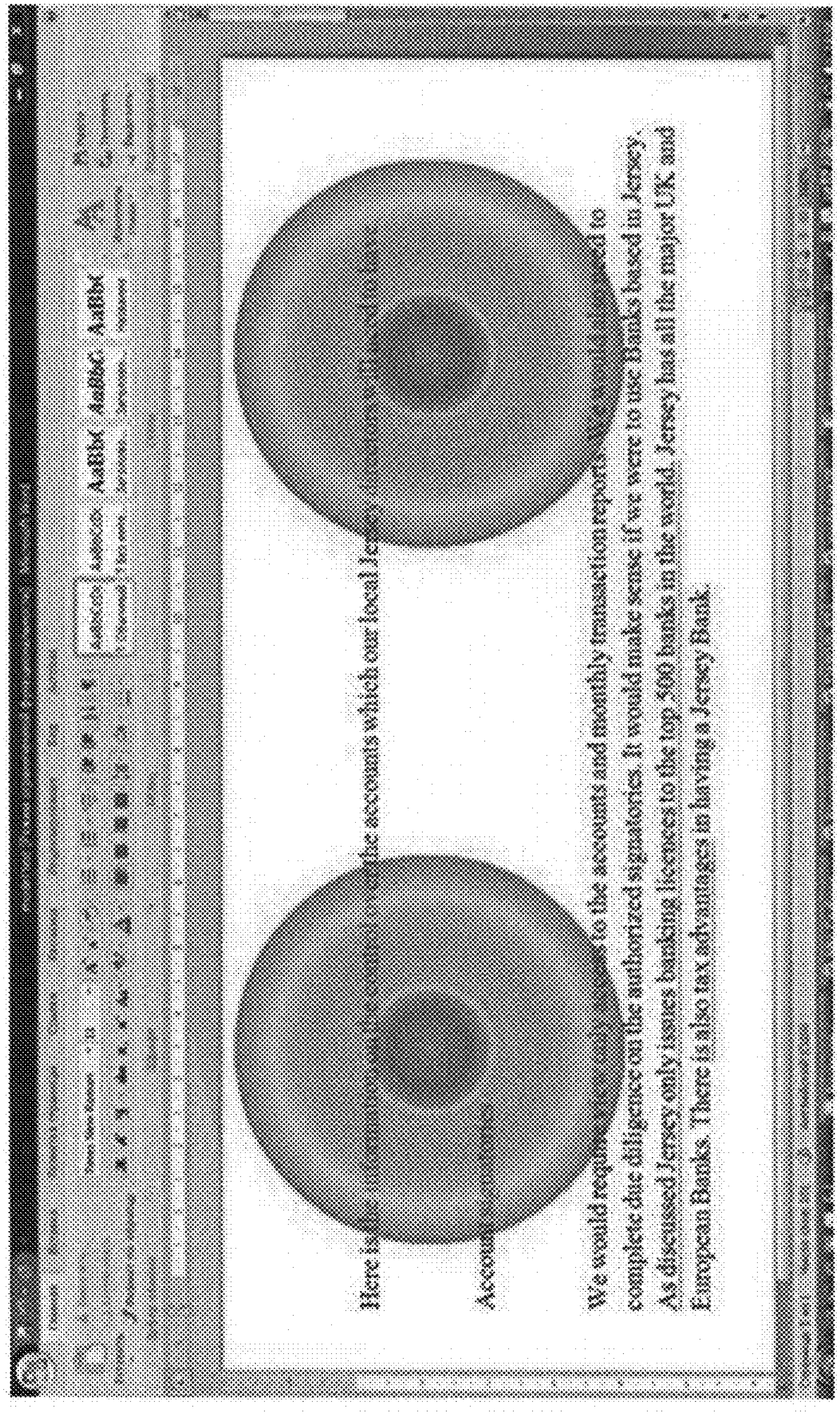
FIG. 4 shows a fourth embodiment in color for the invention.
Figure 5:
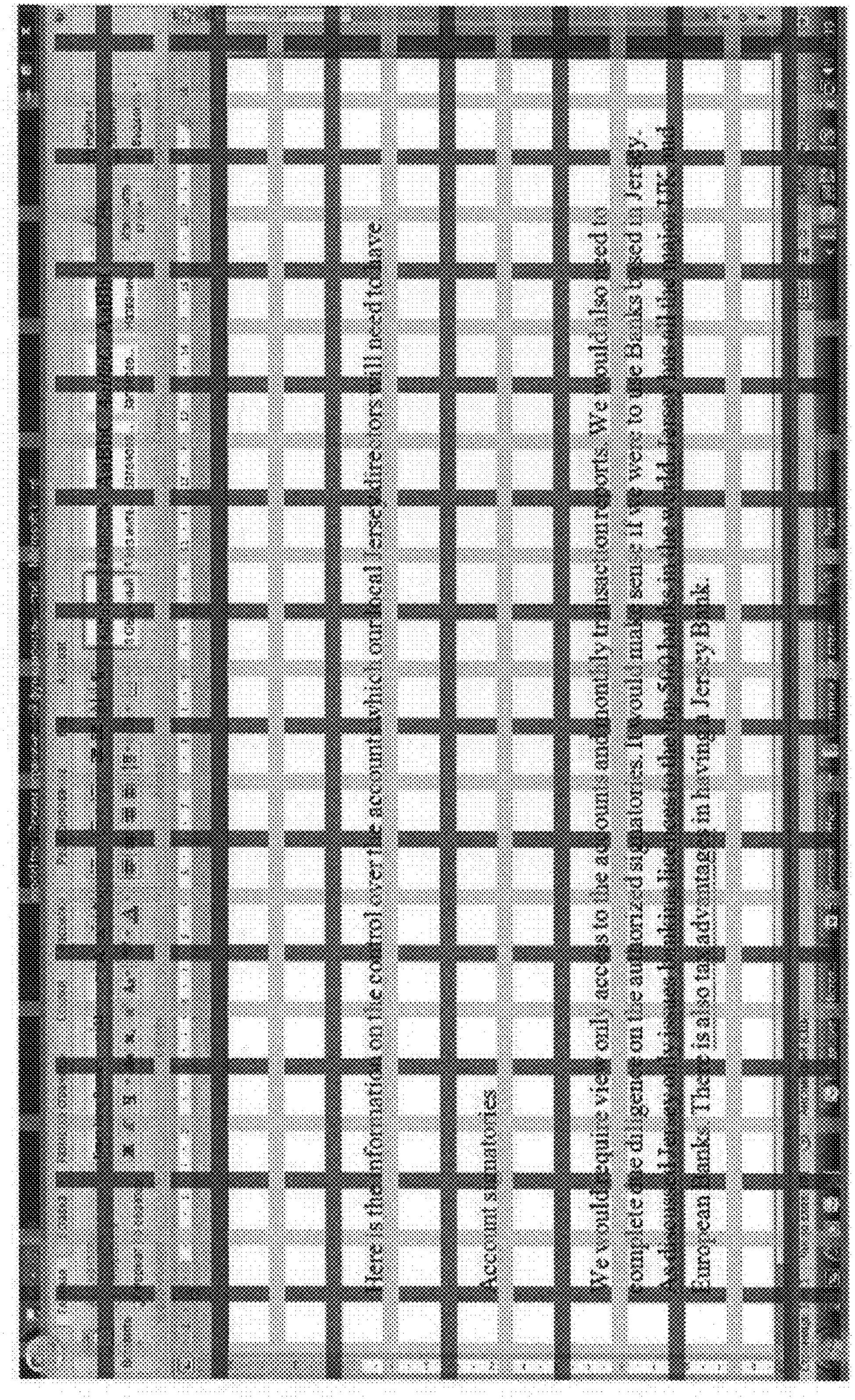
FIG. 5 shows a fifth embodiment in color for the invention.
Figure 6:
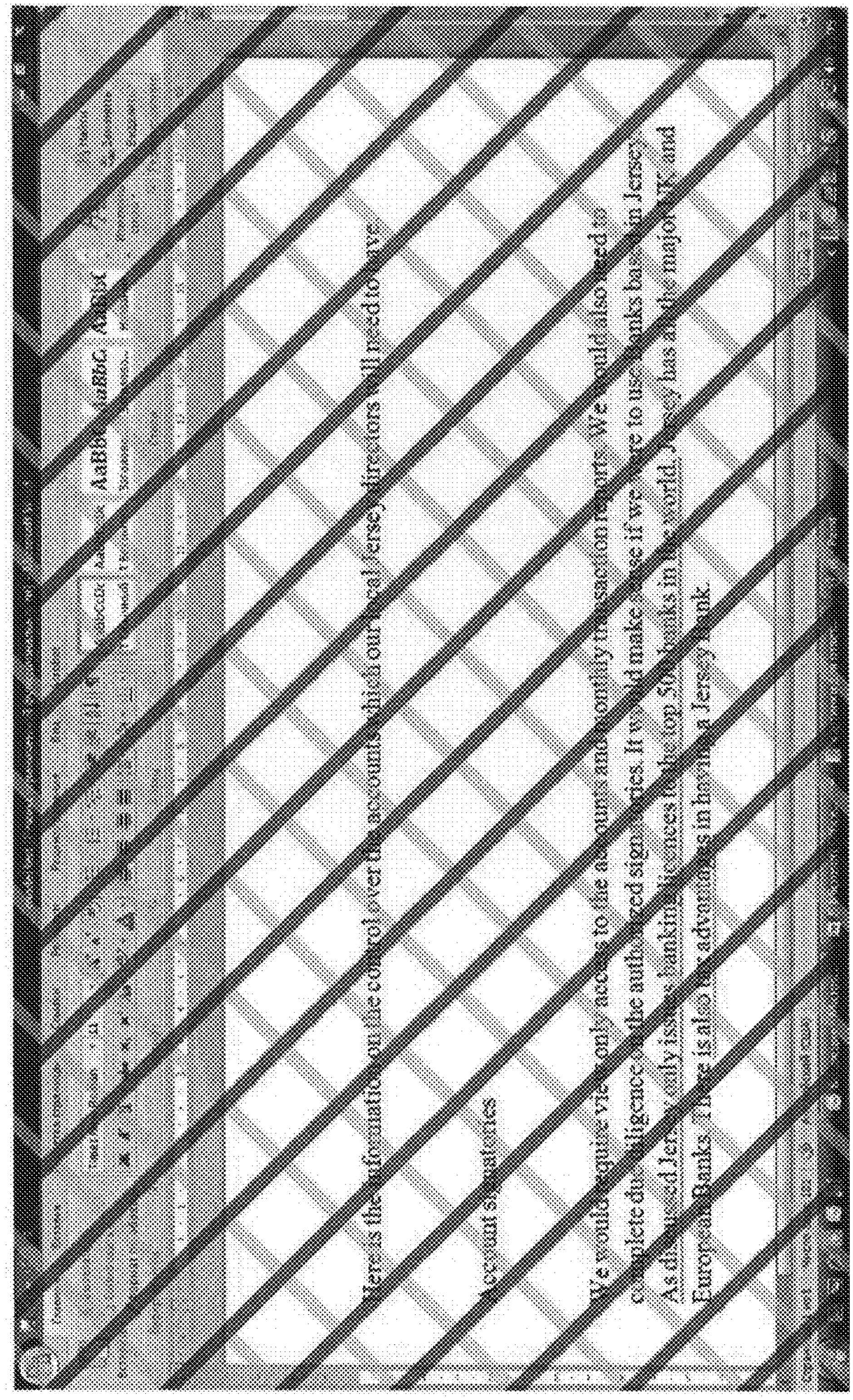
FIG. 6 shows a sixth embodiment in color for the invention.
Figure 7:
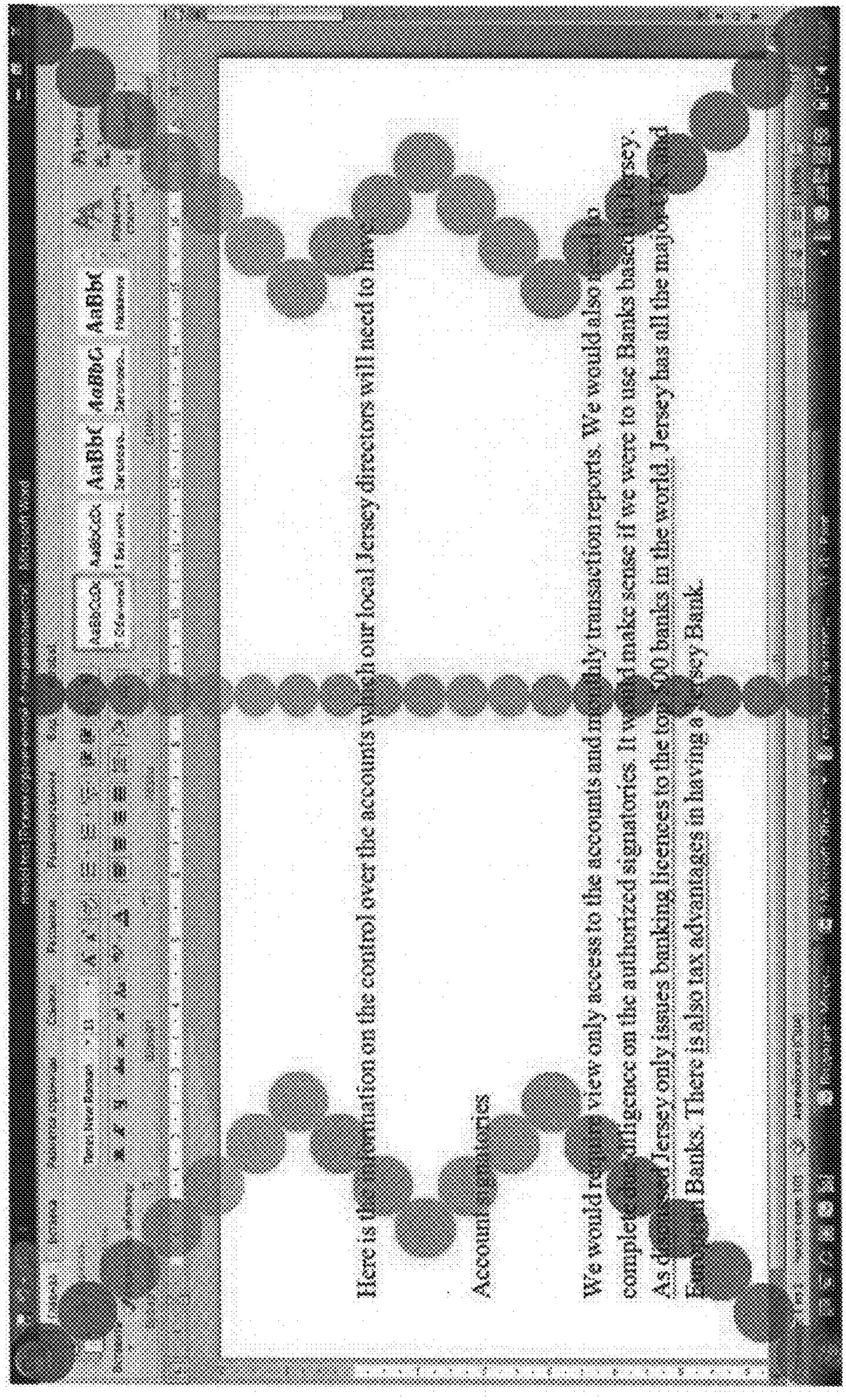
FIG. 7 shows a seventh embodiment in color for the invention.
Figure 8:
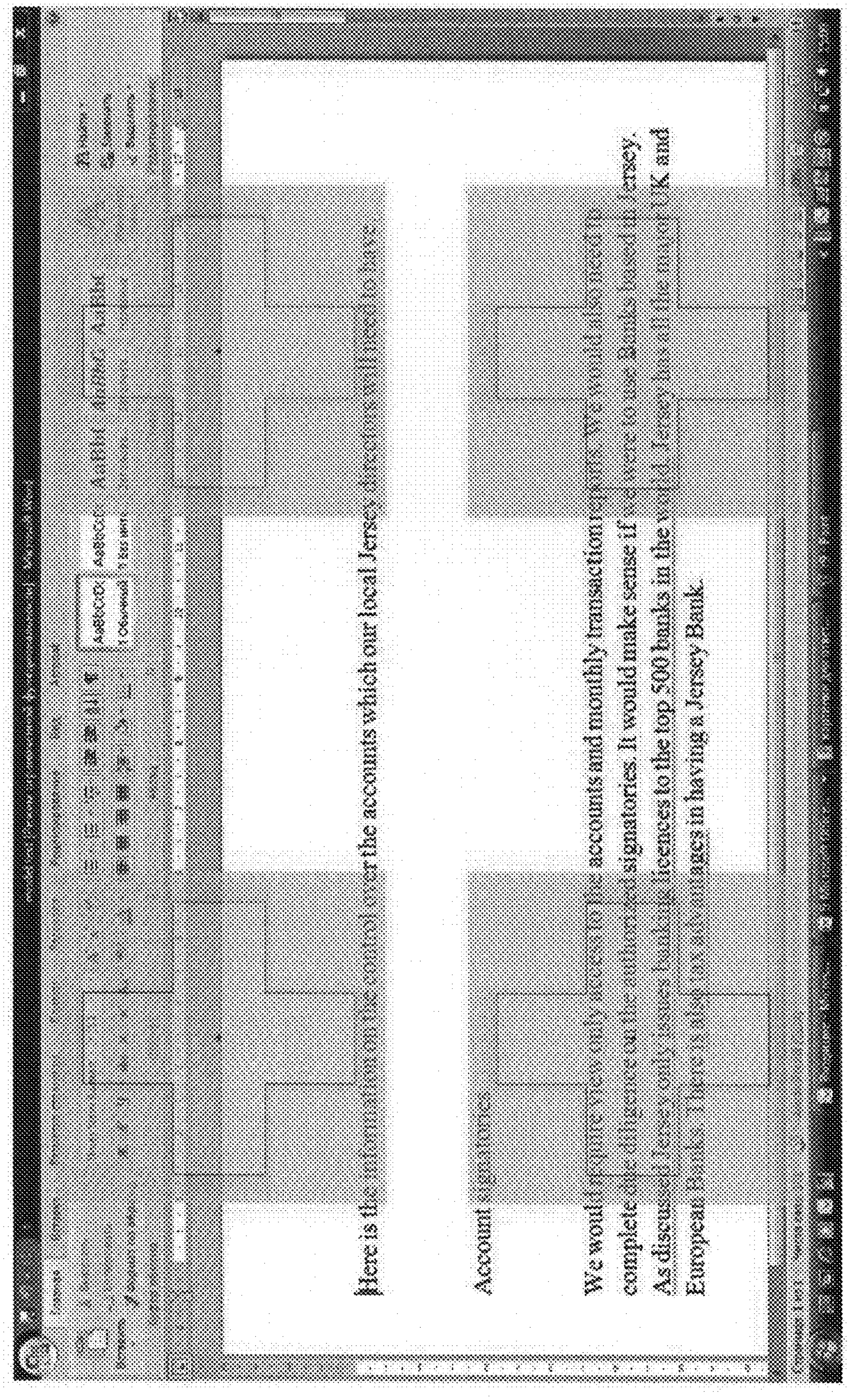
FIG. 8 shows an eighth embodiment in color for the invention.
Figure 9:
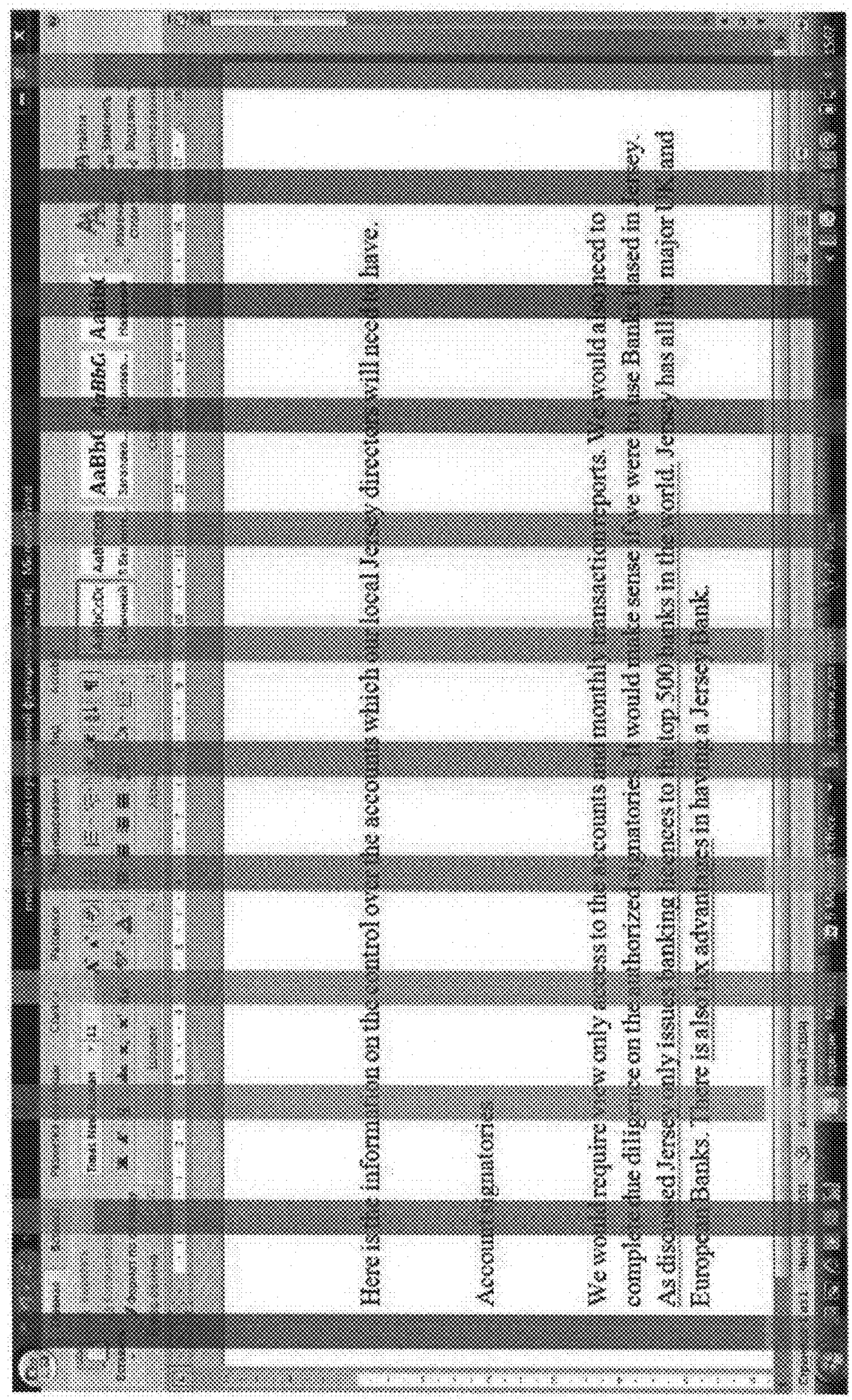
FIG. 9 shows a ninth embodiment in color for the invention.
Figure 10:
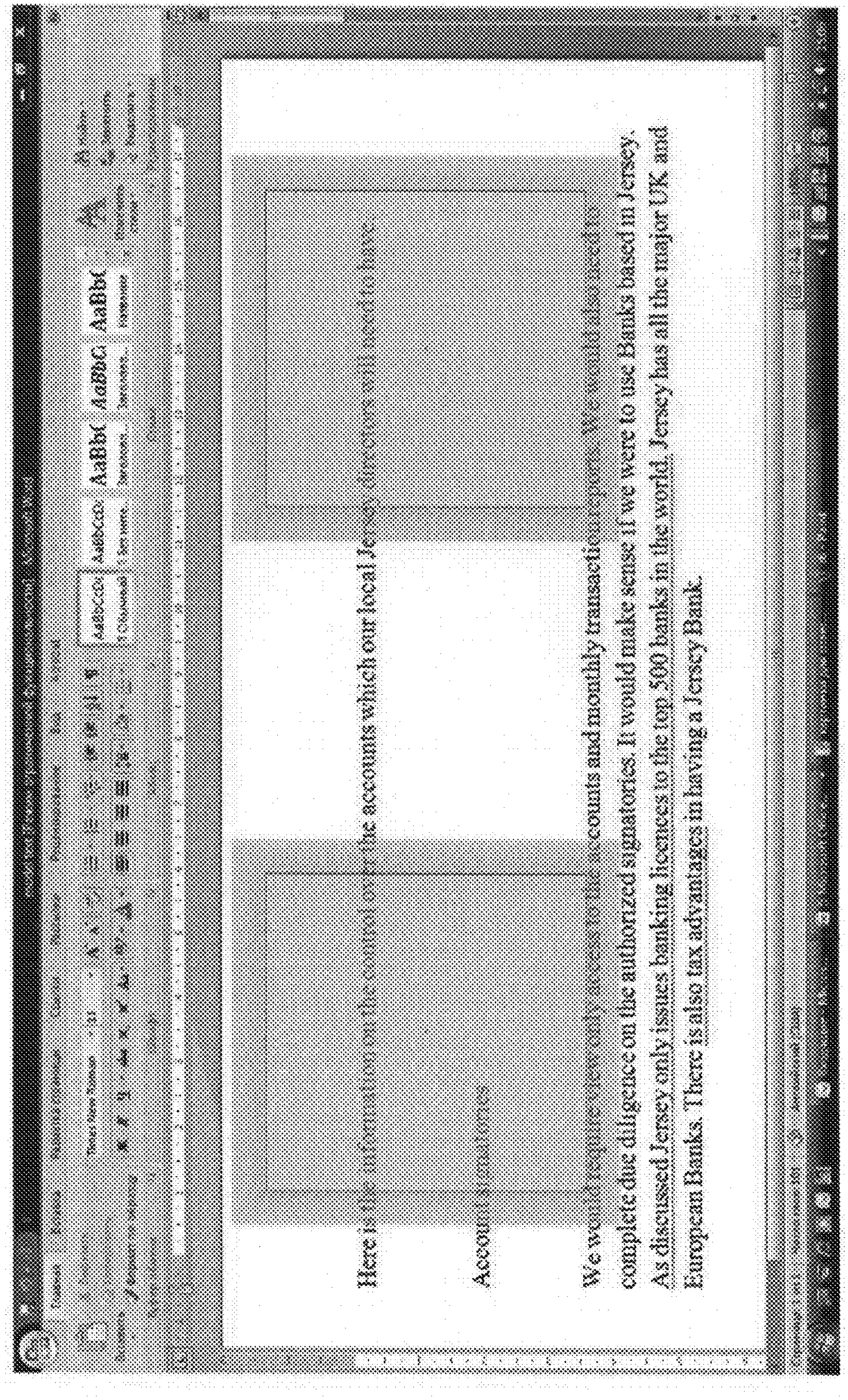
FIG. 10 shows a tenth embodiment in color for the invention.
Figure 11:
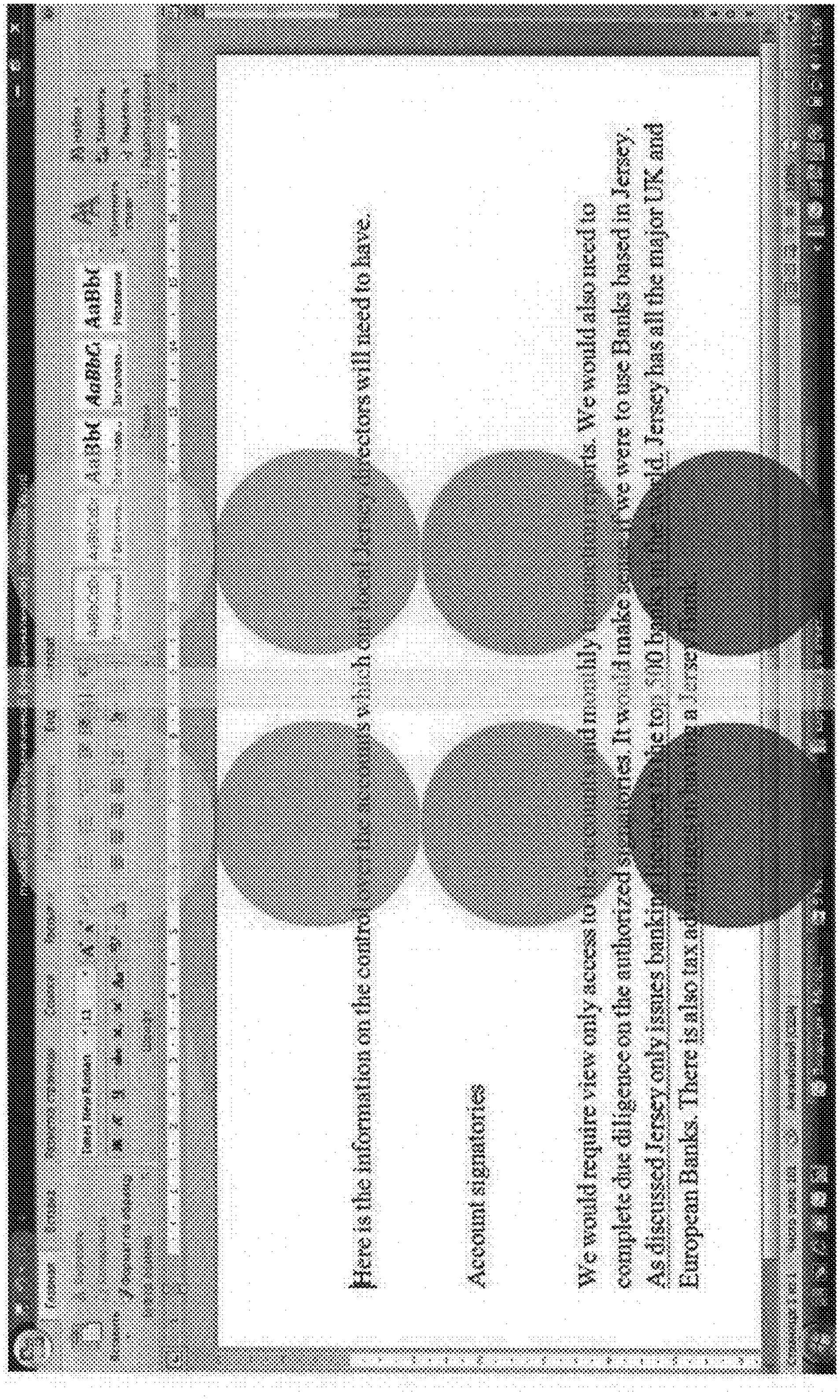
FIG. 11 shows an eleventh embodiment in color for the invention.
Figure 12:
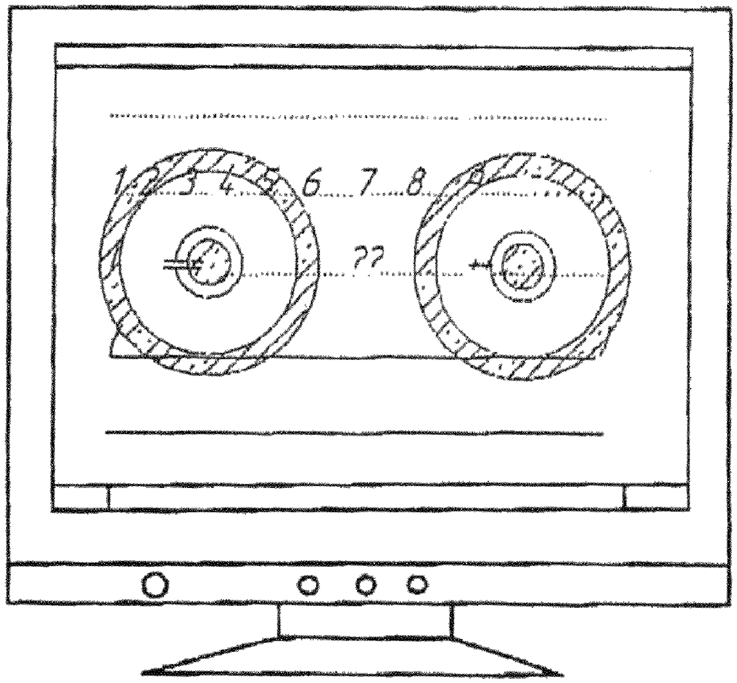
FIG. 12 shows a computer screen with a color pattern similar to that shown in FIG. 4.
Figure 13:
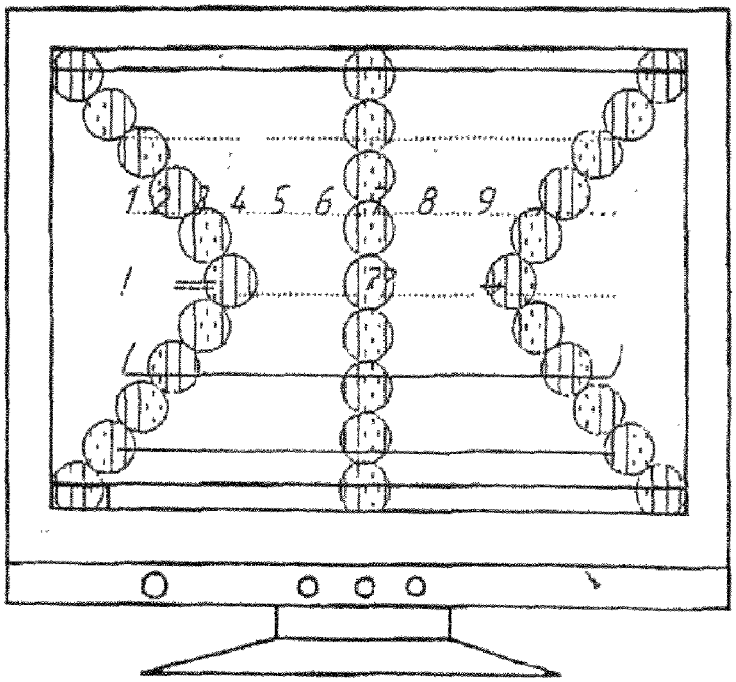
FIG. 13 shows a computer screen with a color pattern similar to that shown in FIG. 7.

FIGS. 1 to 11 show eleven embodiments in color for the present invention. FIG. 12 shows a computer screen with a color pattern similar to that shown in FIG. 4. FIG. 13 shows a computer screen with a color pattern similar to that shown in FIG. 7.

The invention claimed is:

1. A method for preventing deterioration of the sense of sight and/or for mending the sense of sight of a user of display facilities, comprising applying an additional action to the eyes of the user, said action being applied by exposing the user to additional transparent color or black-and-white images on a video screen of said display facilities simultaneously with a text and/or graphics of the main program;

changing position of the images on the screen, or size of the images or color intensity of the images; and duration of said images being selected within a range of 3.0-5.0 minutes and time intervals between the images are selected within a range of 30-50 minutes.

2. A method as claimed in claim 1, wherein said additional images change the color of the text and/or graphics of a main computer program.

3. A method as claimed in claim 1, wherein said additional images are used in the form of a program built into a main computer program.

* * * * *